(12) United States Patent
Miyamoto (10) Patent No.: US 9,737,366 B2
(45) Date of Patent: Aug. 22, 2017

(54) APPARATUS, AND METHOD FOR AIDING DETERMINATION OF A TROCAR PORT POSITION, AND MEDIUM HAVING A TROCAR PORT POSITION DETERMINATION AIDING PROGRAM STORED THEREIN

(71) Applicant: FUJIFILM Corporation, Tokyo (JP)

(72) Inventor: Masaki Miyamoto, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 14/739,647

(22) Filed: Jun. 15, 2015

(65) Prior Publication Data
US 2015/0272692 A1    Oct. 1, 2015

Related U.S. Application Data

(63) Continuation of application No. PCT/JP2013/007399, filed on Dec. 17, 2013.

(30) Foreign Application Priority Data

Dec. 18, 2012    (JP) ................. 2012-275558

(51) Int. Cl.
*G06T 7/70*        (2017.01)
*A61B 34/10*       (2016.01)
(Continued)

(52) U.S. Cl.
CPC ............ *A61B 19/50* (2013.01); *A61B 5/0033* (2013.01); *A61B 5/061* (2013.01);
(Continued)

(58) Field of Classification Search
USPC ............... 345/635, 424, 419; 606/167, 172; 382/128, 131
See application file for complete search history.

(56) References Cited

U.S. PATENT DOCUMENTS 5,417,210 A    5/1995  Funda et al.
8,577,444 B2 * 11/2013 Klingenbeck-Regn  A61B 17/3403
                                              600/424
(Continued)

FOREIGN PATENT DOCUMENTS

| JP | 06-30896 A    | 2/1994 |
| JP | 08-215205 A   | 8/1996 |
| JP | 2006-068301 A | 3/2006 |
| JP | 2011-131020 A | 7/2011 |

OTHER PUBLICATIONS

International Search Report for PCT/JP2013/007399 dated Mar. 4, 2014.

*Primary Examiner* — Chante Harrison
(74) *Attorney, Agent, or Firm* — Sughrue Mion, PLLC (57) ABSTRACT

A point within a three dimensional region represented by volume data is set as a target point. A three dimensional angular range having the target point as its apex is set, and a plurality of line of sight vectors directed toward the target point are set within the three dimensional angular range. A plurality of projected images are generated by projecting the three dimensional region onto projection planes perpendicular to the line of sight vectors for each of the line of sight vectors. The generated projected images are arranged and displayed on a screen.

9 Claims, 5 Drawing Sheets

(51) Int. Cl.
  *A61B 19/00*   (2006.01)
  *A61B 17/34*   (2006.01)
  *G06T 7/00*    (2017.01)
  *A61B 5/00*    (2006.01)
  *A61B 5/06*    (2006.01)
  *A61B 6/03*    (2006.01)
  *A61B 6/12*    (2006.01)

(52) U.S. Cl.
  CPC ...... *A61B 17/3403* (2013.01); *A61B 17/3423* (2013.01); *G06T 7/0012* (2013.01); *G06T 7/70* (2017.01); *A61B 6/032* (2013.01); *A61B 6/12* (2013.01); *A61B 2034/107* (2016.02); *A61B 2560/0475* (2013.01); *G06T 2207/30021* (2013.01); *G06T 2207/30241* (2013.01)

(56) References Cited

U.S. PATENT DOCUMENTS

| | | | |
|---|---|---|---|
| 9,036,882 B2* | 5/2015 | Masumoto | A61B 5/4255 382/128 |
| 2003/0040667 A1* | 2/2003 | Feussner | A61B 5/06 600/407 |
| 2006/0221074 A1 | 10/2006 | Matsumoto | |
| 2012/0327186 A1* | 12/2012 | Kitamura | A61B 1/00009 348/45 |
| 2013/0021336 A1* | 1/2013 | Tsukagoshi | G02B 27/2214 345/419 |
| 2013/0034280 A1* | 2/2013 | Bernhardt | A61B 6/4014 382/128 |
| 2014/0132605 A1* | 5/2014 | Tsukagoshi | A61B 6/466 345/424 |
| 2015/0193966 A1* | 7/2015 | Sakuragi | G06T 19/20 348/46 |

* cited by examiner

APPARATUS, AND METHOD FOR AIDING DETERMINATION OF A TROCAR PORT POSITION, AND MEDIUM HAVING A TROCAR PORT POSITION DETERMINATION AIDING PROGRAM STORED THEREIN

CROSS REFERENCE TO RELATED APPLICATIONS

The present application is a Continuation of PCT International Application No. PCT/JP2013/007399 filed on Dec. 17, 2013, which claims priority under 35 U.S.C. §119(a) to Japanese Patent Application No. 2012-275558 filed on Dec. 18, 2012. Each of the above applications is hereby expressly incorporated by reference, in its entirety, into the present application.

BACKGROUND OF THE INTENTION

Technical Field

The present invention is related to an apparatus, a computer program, and a method for aiding physicians when determining the position of a trocar port during endoscopic surgical procedures performed by inserting surgical instruments and an endoscope through the trocar port.

Background Art

Recently, minimally invasive surgical procedures are becoming widespread in the medical field, in order to reduce the burden on the bodies of patients. In such a surgical procedure, a small hole called a trocar port is formed in the surface of the body of a patient. Surgical instruments and an endoscope are inserted through the trocar port, and treatment is performed while observing a diseased portion and the surgical instruments with the endoscope. In minimally invasive surgical procedures, the range of view and the movable range of the surgical instruments depend greatly on the position of trocar ports. Therefore, whether the position of a trocar port is set appropriately is an important point related to the success or failure of surgical procedures.

Japanese Unexamined Patent Publication No. 2011-131020 discloses a technique for determining the position of a trocar port. In this technique, a physician is prompted to specify the position of a trocar port. A surgical procedure simulation is executed using the specified position. In the case that problems, such as a target portion being outside the range of view of an endo scope and surgical instruments not being able to reach the target portion, occur during the simulation, the physician is prompted to specify the position of the trocar port again. Another surgical procedure simulation is executed using the specified position. The position of a trocar port to be utilized for an actual surgical procedure is determined by repeating the above steps.

DISCLOSURE OF THE INVENTION

In the method disclosed in Japanese Unexamined Patent Publication No. 2011-131020, it is necessary for a physician to repeatedly specify the positions of trocar ports and for surgical procedure simulations to be executed until it is confirmed that the aforementioned problems do not occur in the surgical procedure simulations. Therefore, there is a problem that a long amount of time is required to determine the position of a trocar port.

In addition, in the method disclosed in Japanese Unexamined Patent Publication No. 2011-131020, the process is completed at a point in time at which it is confirmed that the aforementioned problems do not occur in the surgical procedure simulations. That is, the position of the trocar point is determined without considering other candidate points which were not specified by a physician. Therefore, there is a problem that the position of the trocar port which is ultimately determined may not necessarily be the optimal position.

The present invention has been developed in view of the foregoing circumstances. It is an object of the present invention to provide an apparatus, program, and method for aiding determination of a trocar port position for preoperative planning of endoscopic surgical procedures which are performed by inserting surgical instruments and an endoscope through a trocar port, that enables expedient and simple determination of an optimal trocar point position.

A trocar port position determination aiding apparatus of the present invention comprises:

volume data storing means for storing volume data obtained by imaging a subject;

target point setting means for setting a point within a three dimensional region represented by the volume data as a target point;

line of sight setting means for setting a three dimensional angular range having the target point as an apex and for setting a plurality of line of sight vectors within the three dimensional angular ranges directed toward the target point; and projected image display means for generating a plurality of projected images by projecting the three dimensional regions onto projection planes perpendicular to each of the plurality of line of sight vectors, and for displaying the plurality of projected images such that they are arranged on a screen.

The trocar port position determination aiding apparatus of the present invention may further comprise: obstacle region storing means for storing obstacle regions which are set in advance as regions that will become obstacles in ranges of view within the three dimensional region, and obstacle judging means for judging whether each of the plurality of line of sight vectors pass through the obstacle regions or pass through the vicinities of the obstacle regions. In this case, the projected image display means may display projected images generated for line of sight vectors which have been judged to pass through the obstacle regions or the vicinities thereof and projected images generated for line of sight vectors which has been judged to not pass through the obstacle regions or the vicinities thereof in a visually distinguishable manner.

The line of sight setting means may detect a user operation that specifies a portion of the plurality of projected images, which are displayed on the screen, that includes two or more of the projected images, and resets a plurality of line of sight vectors directed toward target points within a portion of the three dimensional angular range that includes the line of sight vectors of the portion of the projected images specified by the user operation and include line of sight vectors different from the line of sight vectors of the portion of the projected images. In this case, the projected image display means may generate a plurality of projected images by projecting the three dimensional region onto projection planes perpendicular to each of the plurality of reset line of sight vectors, and display the plurality of newly generated projected images such that they are arranged on the screen.

At this time, in the case that the plurality of reset line of sight vectors include line of sight vectors which had been previously set, it is not necessary for projected images to be newly generated for these line of sight vectors, and the projected images which had been generated previously for these line of sight vectors may be employed.

The line of sight setting means may set a plurality of base points within a portion of a spherical plane having a predetermined radius and the target point within the three dimensional angular range as its center, and set vectors directed toward the target point from each of the plurality of base points as the plurality of line of sight vectors. In this case, the projected image display means may generate the plurality of projected images by transmissive projection using the plurality of the set base points as viewpoints.

The target point setting means may generate a two dimensional tomographic image or a pseudo three dimensional image based on the volume data, display the generated image on the screen, detect a user operation that specifies a point within the two dimensional tomographic image or the pseudo three dimensional image on the screen, and set a point within the three dimensional region corresponding to the point specified by the user operation as the target point.

The line of sight setting means may generate at least one two dimensional tomographic image that passes through the target point, based on the volume data, detect a user operation that specifies an angular range having the target point within the at least one two dimensional tomographic image as a peak, and set the three dimensional angular range based on the angular range specified by the user operation.

A trocar port position determination aiding program of the present invention is loaded into one or a plurality of computers, and causes the computer or computers to function as the aforementioned target point setting means, the line of sight setting means, the projected image display means, etc. The program is constituted by a plurality of program modules, and the processes performed by each of the aforementioned means are executed by one or a plurality of program modules. The group of program modules is provided to users by being recorded in recording media such as CD-ROM's and DVD's, recorded in the storage of a server computer, or recorded in network storage in a downloadable state.

A trocar port position determination aiding method of the present invention is a method that aids determination of the position of a trocar port, comprising a target point setting process that sets a point within a three dimensional region represented by volume data, which are obtained by imaging a subject and are stored in a storage device, as a target point; a line of sight setting process that sets a three dimensional angular range having the target point as an apex and sets a plurality of line of sight vectors within the three dimensional angular ranges directed toward the target point; and a projected image display process that generates a plurality of projected images by projecting the three dimensional regions onto projection planes perpendicular to each of the plurality of line of sight vectors, and displays the plurality of projected images such that they are arranged on a screen, executed by one or a plurality of computers.

The apparatus, program, and method for aiding determination of a trocar port position of the present invention set a point within a three dimensional region represented by volume data, which are obtained by imaging a subject and are stored in a storage device, as a target point; set a three dimensional angular range having the target point as an apex and set a plurality of line of sight vectors within the three dimensional angular ranges directed toward the target point; and generate a plurality of projected images by projecting the three dimensional regions onto projection planes perpendicular to each of the plurality of line of sight vectors, and display the plurality of projected images such that they are arranged on a screen. Therefore, visual ranges for cases in which trocar ports are set at a plurality of candidate positions for trocar ports can be displayed together and provided to a physician, particularly by setting a point within a three dimensional region corresponding to a target site for a surgical procedures as the target point and by setting a three dimensional angular range that covers a region of a body surface in which trocar ports are capable of being set with respect to the target site for the surgical procedure. Thereby, the physician can comprehensively confirm and consider the visual range of each of the candidate positions for a trocar port by viewing the displayed visual ranges. As a result, an optimal position for a trocar port can be expediently and easily determined.

The apparatus, program, and method for aiding determination of a trocar port position of the present invention may store obstacle regions which are set in advance as regions that will become obstacles in ranges of view within the three dimensional region, judge whether each of the plurality of line of sight vectors pass through the obstacle regions or pass through the vicinities of the obstacle regions, and display projected images generated for line of sight vectors which have been judged to pass through the obstacle regions or the vicinities thereof and projected images generated for line of sight vectors which has been judged to not pass through the obstacle regions or the vicinities thereof in a visually distinguishable manner. In this case, a physician can expediently see candidate positions, which are clearly inappropriate as positions for a trocar port due to the central portions of the visual ranges being obstructed by obstacle regions, and other candidate positions. As a result, the targets of consideration can be narrowed, and operational efficiency can be improved.

In addition, the apparatus, program, and method for aiding determination of a trocar port position of the present invention may detect a user operation that specifies a portion of the plurality of projected images, which are displayed on the screen, that includes two or more of the projected images, reset a plurality of line of sight vectors directed toward target points within a portion of the three dimensional angular range that includes the line of sight vectors of the portion of the projected images specified by the user operation and include line of sight vectors different from the line of sight vectors of the portion of the projected images, generate a plurality of projected images by projecting the three dimensional region onto projection planes perpendicular to each of the plurality of reset line of sight vectors, and display the plurality of newly generated projected images arranged on a screen. In this case, a physician can first see a range that includes candidate positions for trocar ports which are considered to be comparatively appropriate within the entirety of the three dimensional angular range, narrow down considerations to within this range and perform more detailed consideration. As a result, the position of an optimal position for a trocar port can be found more expediently and simply.

BEST MODE FOR CARRYING OUT THE INVENTION

Hereinafter, embodiments of the apparatus, program, and method for aiding determination of a trocar port position will be described in detail with reference to the attached drawings. In the embodiments to be described below, the trocar port position determination aiding apparatus is a computer, in which the trocar port position determination aiding program is installed. The trocar port position determination aiding program is distributed recorded in a recording medium such as a CD-ROM and a DVD, and installed in the computer from the recording medium. Alternatively, the trocar port position determination aiding program is recorded in the storage of a server computer connected to a network, or recorded in network storage in a state accessible from the exterior. In this case, the trocar port position determination aiding program is downloaded to a computer to be utilized by a physician and installed as necessary.

Figure 1:
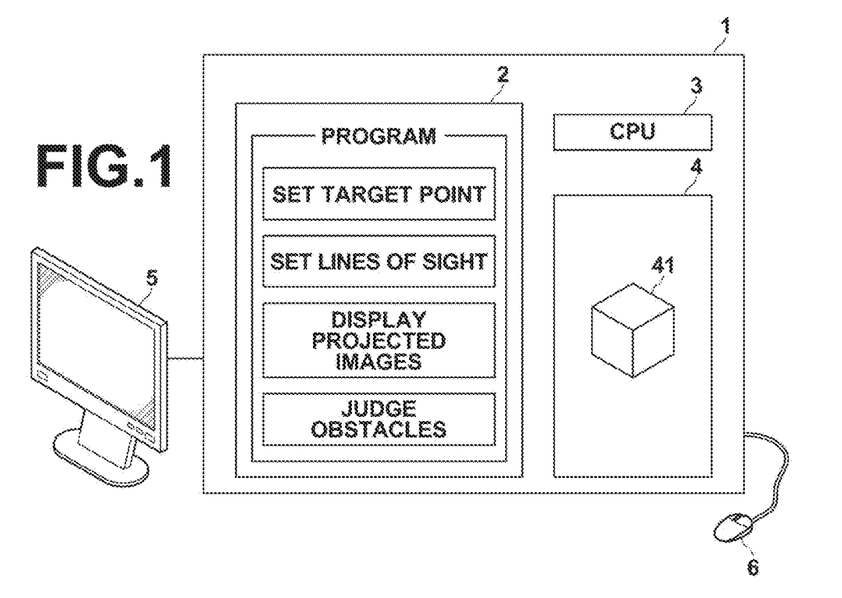
FIG. 1 is a diagram that illustrates the schematic configuration of a trocar port position determination aiding apparatus according to an embodiment of the present invention.

FIG. 1 is a diagram that illustrates the schematic configuration of a trocar port position determination aiding apparatus 1, which is realized by installing the trocar port position determination aiding program into a computer. As illustrated in FIG. 1, the trocar port position determination aiding apparatus 1 is equipped with a memory 2, a CPU 3, and a storage 4. In addition, a display 5 and an input device such as a mouse 6 are connected to the trocar port position determination aiding apparatus 1.

The storage 4 (volume data storing means, obstacle region storing means) has volume data obtained by imaging subjects stored therein. Volume data obtained by reconstituting slice data output by tomographic imaging apparatuses such as a CT apparatus and an MRI apparatus, volume data output by three dimensional imaging apparatuses such as a 3DCT apparatus and a cone beam CT apparatus, and the like, are stored in the storage 4, for example.

In addition, data that specify regions within a three dimensional region represented by the volume data 41 that will be obstacles to visual fields are stored as obstacle regions in the storage 4. Data that specify bone regions and major blood vessel regions are stored in the storage 4 as obstacle regions, for example. The obstacle regions may be regions which are extracted by analyzing the volume data based on keywords (for example, "bone", etc.) which are input by a user or set as default keywords. Alternatively, the obstacle regions may be regions which are directly specified by a user within a screen that displays the three dimensional region represented by the volume data.

In addition, a trocar port position determination aiding program is stored in the memory 2. The trocar port position determination aiding program define a target point setting process, a line of sight setting process, a projected image display process, an obstacle judging process, etc. as processes to be executed by the CPU 3. The computer functions as a target point setting means, a line of sight setting means, a projected image display means, an obstacle judging means, etc. by the CPU 3 executing these processes according to the program.

Hereinafter, the specific processes performed by the trocar port position determination aiding apparatus 1 will be described. The trocar port position determination aiding apparatus 1 loads volume data 41 of a subject, which is stored in the storage 4, into the memory 2 when it is detected that a trocar port position determination aiding function has been selected from a menu.

Figure 2:
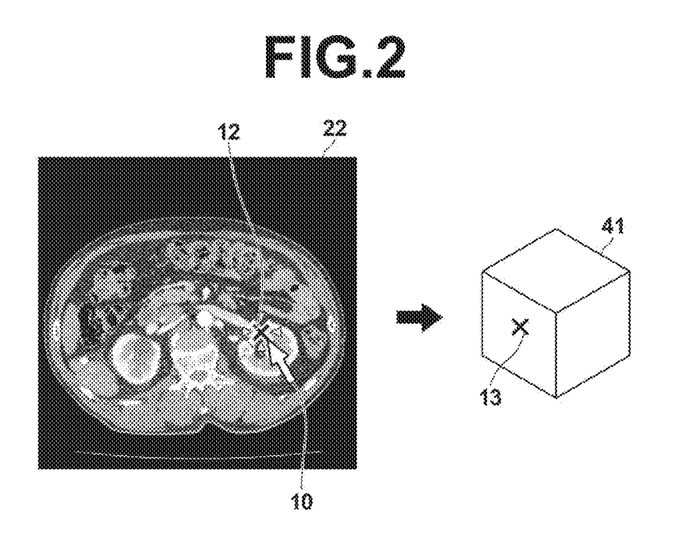
FIG. 2 is a diagram for explaining a method by which a target point is set.

Next, the trocar port position determination aiding apparatus 1 executes a target point setting process that sets a point within a three dimensional region (hereinafter, referred to as "three dimensional region D") represented by the volume data 41 as a target point. The target point may be set manually or automatically. In the case that the target point is set manually, a two dimensional tomographic image such as an axial image, a sagittal image, and a coronal image, or a volume rendered pseudo three dimensional image is generated based on the volume data 41. The generated image is displayed on the screen of the display 5, and mouse operations by a user with respect to the screen are detected. The position of a point 12 specified by a cursor 10 within the two dimensional image or the pseudo three dimensional image is obtained, and a point 13 within the three dimensional region D corresponding to the obtained position is set as the target point. FIG. 2 is a diagram that illustrates an example in which an axial two dimensional tomographic image 22 is displayed on the screen, specification of a point 12 within the screen is received, and the position of a point 13 is specified within the three dimensional region D as a target point.

In the case that the target point is set automatically, the trocar port position determination aiding apparatus 1 detects a characteristic portion such as a lesion, which is a target portion for a surgical procedure, by analyzing the volume data 41, and sets a point that represents the position of the characteristic portion within the volume data as the target point. Various automatic detecting methods which are utilized in known CAD (Computer Aided Diagnosis) systems may be employed to detect the characteristic portion. Note that with respect to the setting of the target point, manual setting and automatic setting may be selectively executed by selection from a menu.

Next, the trocar port position determination aiding apparatus 1 executes a line of sight setting process that sets a three dimensional angular range having the target point 13 as its apex, and sets a plurality of line of sight vectors Vij (i and j are natural numbers) directed toward the target point 13 within the three dimensional angular range. In the line of sight setting process, first, at least one two dimensional tomographic image that passes through the target point 13 is generated based on the volume data 41. The at least one generated two dimensional tomographic image is displayed on the screen, and a user operation that specifies a fan shaped angular range having the target point 13 as the apex within the at least one two dimensional image is detected. A conical or a pyramid shaped three dimensional angular range is set based on the angular range specified by the user operation.

Figure 3:
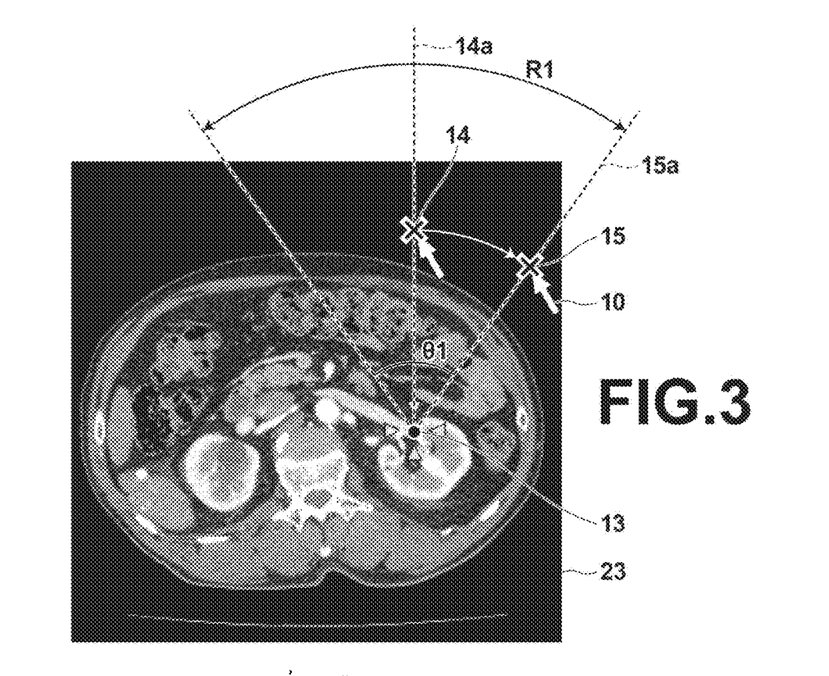
FIG. 3 is a diagram for explaining a method by which an angular range is set.
Figure 4:
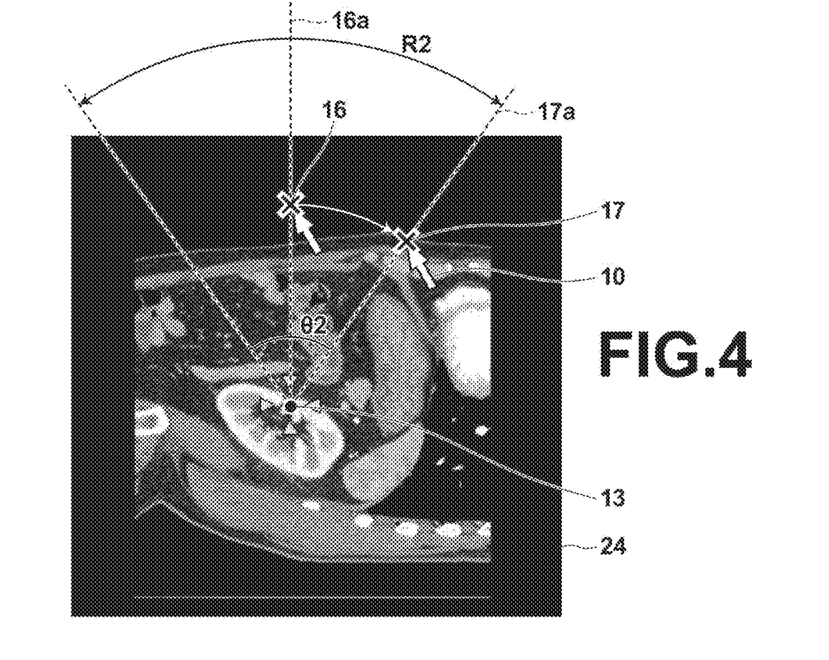
FIG. 4 is a diagram for explaining a method by which an angular range is set.
Figure 5:
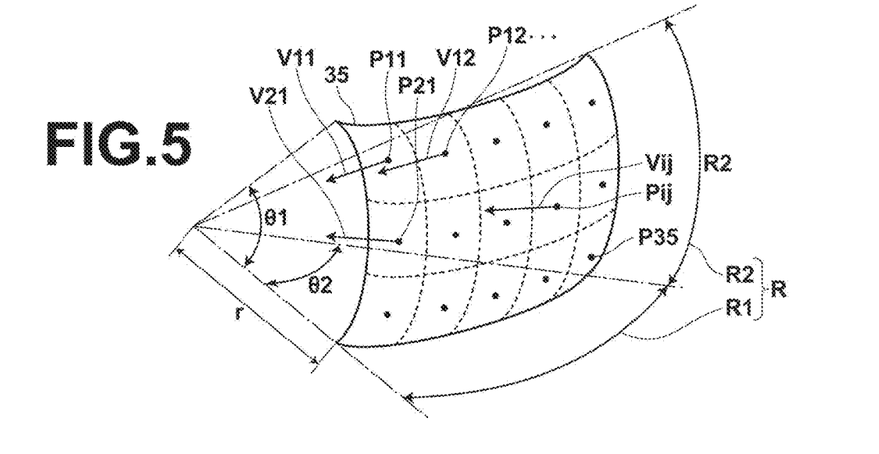
FIG. 5 is a diagram for explaining a method by which line of sight vectors are set.

For example, an axial two dimensional tomographic image 23 such as that illustrated in FIG. 3 is displayed on the screen of the display 5. Mouse operations by a user that sequentially specify points 14 and 15 within the two dimensional tomographic image 23 on the screen are detected. Then, an angular range R1, which is an angular range between a central reference line 14a having the target point 13 as a starting point and passes through the point 14 and a range setting line 15a having the target point 13 as a starting point and passes through the point 15 and an angular range between the central reference line 14a and a line opposite the range setting line 15a in the circumferential direction having the same angular spread, is obtained. In addition, a sagittal two dimensional tomographic image 24 such as that illustrated in FIG. 4 is displayed on the screen of the display 5. Mouse operations by a user that sequentially specify points 16 and 17 within the two dimensional tomographic image 24 on the screen are detected. Then, an angular range R2, which is an angular range between a central reference line 16a having the target point 13 as a starting point and passes through the point 16 and a range setting line 17a having the target point 13 as a starting point and passes through the point 17 and an angular range between the central reference line 16a and a line opposite the range setting line 17a in the circumferential direction having the same angular spread, is obtained. A three dimensional angular range R having the angular range R1 in the circumferential direction of an axial cross section and the angular range R2 in the circumferential direction of a sagittal cross section is set based on the specified angular ranges R1 and R2, as illustrated in FIG. 5.

Next, a plurality of line of sight vectors Vij (i and j are natural numbers) directed toward the target point 13 are set within the set three dimensional angular range R. For example, a partial region 35 of a spherical plane having a radius r and the target point 13 as its center may be set within the three dimensional angular range R as illustrated in FIG. 5. The region 35 may be divided into 15 adjacent substantially equal divided regions in 3 rows and 5 columns. One base point Pij (i=1~3, j=1~5) is set in each of the divided regions, and a plurality of line of sight vectors Vij directed toward the target point 13 from each of the plurality of base points Pij are set. Thereby, 15 line of sight vectors Vij, which are adjacent to each other at substantially equidistant intervals and arranged in 3 rows and 5 columns, are set within the three dimensional angular range R. Note that the size of the radius r may be set and corrected by a user as desired.

Next, the trocar port position determination aiding apparatus 1 projects three dimensional regions D onto projection planes perpendicular to the directions of each of the line of sight vectors Vij which have been set in the line of sight setting process, to generate a plurality of projected images Sij (i=1~3, j=1~5), and executes a projected image display process that arranges and displays the projected images Sij on the screen. The technique used to project the three dimensional regions D may be the transmissive projection (central projection) technique or the parallel projection technique. In the case that the transmissive projection technique is employed, a plurality of projected images Sij having the plurality of base points Pij which are set in the region 35 as viewpoints are generated. In addition, when generating the projected images, a target organ region that includes the target portion, other major organ regions in the periphery of the target portion, bone regions, etc. may be specified in advance and stored by analyzing the three dimensional region D. Display parameters such as opacity values suited for the generation of desired projected images may be set based on the information stored in this manner.

Figure 6:
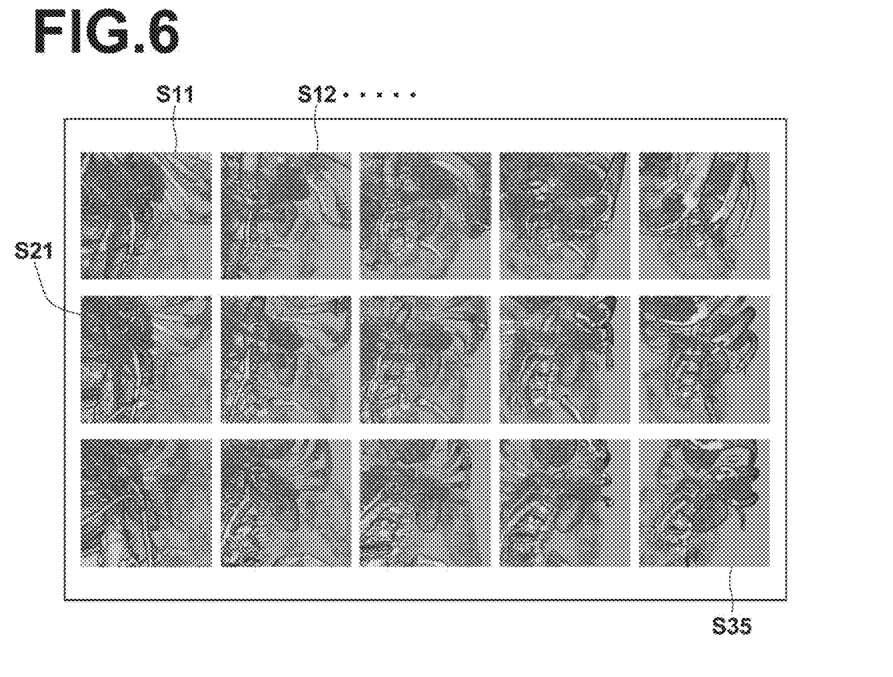
FIG. 6 is a diagram that illustrates a first example of a screen on which projected images are arranged and displayed.

In addition, when displaying the plurality of projected images Sij on the screen, physicians will be able to substantially understand the line of sight directions of projected images that they are viewing when referring to the arranged display of the projected images, by arranging the projected images Sij at positions corresponding to the positional relationships among the line of sight vectors Vij. FIG. 6 is a diagram that illustrates an example of a screen on which the trocar port position determination aiding apparatus 1 has displayed a plurality of projected images Sij. In the example of FIG. 6, the plurality of projected images Sij are arranged in three rows and five columns corresponding to the three rows and five columns of the plurality of line of sight vectors Vij.

Figure 7:
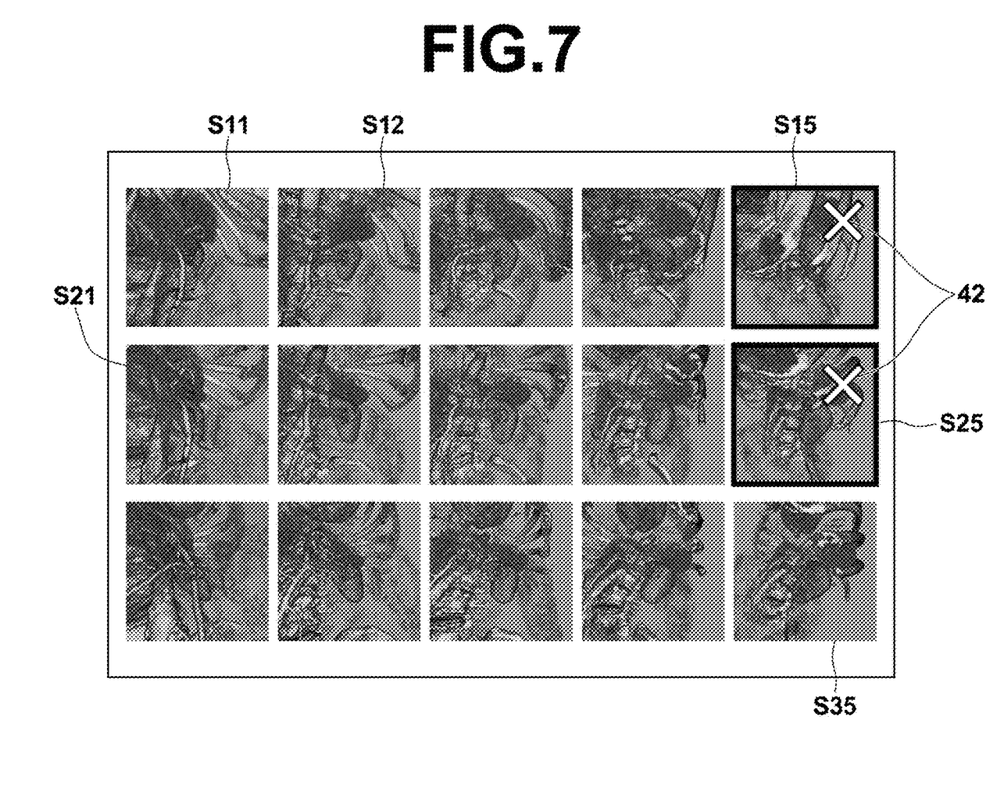
FIG. 7 is a diagram that illustrates a second example of a screen on which projected images are arranged and displayed.

In addition, the trocar port position determination aiding apparatus 1 may refer to the data regarding obstacle regions stored in the storage when displaying the plurality of projected images Sij on the screen. The trocar port position determination aiding apparatus 1 may next judge whether each of the line of sight vectors Vij passes through an obstacle region or the vicinity thereof, that is, whether an obstacle region is located at the central portion of the visual range (corresponding to the central portion of an image). The trocar port position determination aiding apparatus 1 may then display projected images generated for line of sight vectors which have been judged to pass through the obstacle regions or the vicinities thereof and projected images generated for line of sight vectors which has been judged to not pass through the obstacle regions or the vicinities thereof the obstacle regions in a visually distinguishable manner. For example, x shaped marks 42 may be displayed on projected images S15 and S25, generated for line of sight vectors which have been judged to pass through obstacle regions or the vicinities thereof, from among all of the projected images Sij which are displayed on the screen, as illustrated in FIG. 7. Note that the trocar port position determination aiding apparatus 1 may be configured such that the function of displaying the projected images in the visually distinguishable manner may be turned ON and OFF by a user as desired.

In addition, if the trocar port position determination aiding apparatus 1 detects mouse operations by a user that specify a portion of the plurality of projected images Sij, which are displayed on the screen, that includes two or more of the projected images, the trocar port position determination aiding apparatus 1 executes a line of sight setting process that resets a plurality of line of sight vectors directed toward target points within a portion of the three dimensional angular range that includes the line of sight vectors of the portion of the projected images specified by the user operation and include line of sight vectors different from the line of sight vectors of the portion of the projected images. Then, the trocar port position determination aiding apparatus 1 further executes a projected image display process that generates a plurality of projected images for each of the plurality of reset line of sight vectors, and display the plurality of newly generated projected images such that they are arranged on the screen.

Figure 8:
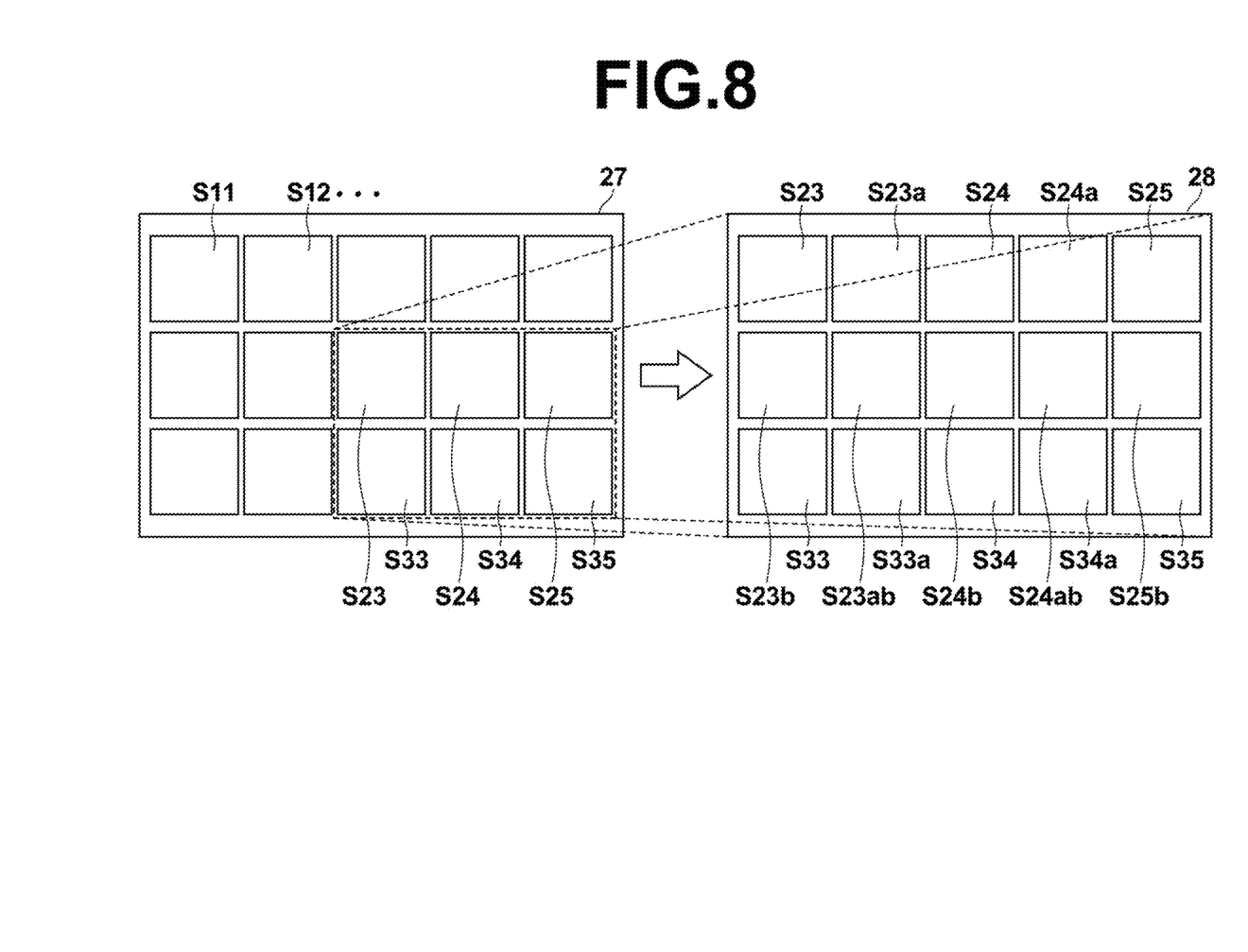
FIG. 8 is a diagram for explaining a method by which projected images are narrowed down and displayed.

For example, mouse operations by a user may specify six projected images S23 through S25 and S33 through S35, which are adjacent to each other in two rows and three columns on a screen 27 on which 15 projected images Sij are displayed, as illustrated in the left side of FIG. 8. The trocar position determination aiding apparatus 1 may switch display to a screen 28 having plurality of newly generated projected images within a range narrowed down to the specified portion of images in response to this user operation, as illustrated in the right side of FIG. 8. In the example of FIG. 8, new line of sight vectors are additionally set at intermediate points between pairs of adjacent vectors within a range of the portion that includes the six projected images specified in the screen 27. Then, newly generated projected images S23a, S24a, S23b, S23ab, . . . and the previously generated projected images S23 through S25 and S33 through S35 are displayed on the screen in an arrangement corresponding to the positional relationships among the line of sight vectors.

According to the configuration of the apparatus, program, and method for aiding determination of a trocar port position of the present invention described above, a physician can comprehensively confirm and consider the visual range of each of a plurality of candidate positions for a trocar port, based on the arranged display of visual ranges for cases in which a trocar port is set at each of the candidate positions for a trocar port. As a result, an optimal position for a trocar port can be expediently and easily determined.

Note that the above embodiment was described as a case in which a central reference line and an angle of spread (θ1 in FIG. 3, and θ2 in FIG. 4) are set in response to mouse operations by a user that specify two points (for example, the points 14 and 15 in FIG. 3) within the two dimensional tomographic image 23 when setting the three dimensional angular range having the target point 13 as its apex. Alternatively, a configuration may be adopted, in which a default angle of spread is set in advance, an angular range determined by the default angle is displayed on the screen when a user operation specifies a central reference line, and a user changes the angle of spread by mouse operations in this screen as necessary.

In addition, the above embodiment was described as a case in which 15 adjacent line of sight vectors arranged in 3 rows and 5 columns are set. However, the number and distribution of the line of sight vectors is not limited to those of the above embodiment. The number and distribution of the line of sight vectors may be set as desired according to the number of projected images which is capable of being simultaneously displayed on a screen, the shape and size of the three dimensional angular range, etc.

Further, the processes which are executed by the trocar port position determination aiding apparatus, which is a single computer in the above embodiment, may be distributed and executed by a plurality of computers.

As described above, the present invention is not limited to the above embodiment. Various changes and modifications are possible as long as they do not stray from the spirit and scope of the present invention.

What is claimed is:

1. A non-transitory computer readable recording medium having a trocar port position determination aiding program stored therein, the trocar port position determination aiding program causing one or a plurality of computers to execute:
a first setting instruction of setting a point within a three dimensional region represented by the volume data, which are obtained by imaging a subject and are stored in a storage device, as a target point;
a second setting instruction of setting a three dimensional angular range having the target point as an apex and for setting a plurality of line of sight vectors within the three dimensional angular ranges directed toward the target point; and
a generating and displaying instruction of generating a plurality of projected images by projecting the three dimensional regions onto projection planes perpendicular to each of the plurality of line of sight vectors, and displaying the plurality of projected images such that they are arranged on a screen in an arrangement that corresponds to the positional relationships among the line of sight vectors, wherein the first setting instruction further comprises:
storing obstacle regions which are set in advance as regions that will become obstacles in ranges of view within the three dimensional region; and
judging whether each of the plurality of line of sight vectors pass through the obstacle regions or pass through the vicinities of the obstacle regions, and
wherein the displaying instruction displays projected images generated for line of sight vectors which have been judged to pass through the obstacle regions or the vicinities thereof in a visually distinguishable manner from projected images generated for line of sight vectors which have been judged to not pass through the obstacle regions or the vicinities thereof,
wherein the visually distinguishable manner comprises at least one of emphasizing and marking.

2. A trocar port position determination aiding method, comprising: a target point setting process, executed by at least one computer, that sets a point within a three dimensional region represented by volume data, which are obtained by imaging a subject and are stored in a storage device, as a target point;
a line of sight setting process, executed by the at least one computer, that sets a three dimensional angular range having the target point as an apex and sets a plurality of line of sight vectors within the three dimensional angular ranges directed toward the target point; and
a projected image display process, executed by the at least one computer, that generates a plurality of projected images by projecting the three dimensional regions onto projection planes perpendicular to each of the plurality of line of sight vectors, and displays the plurality of projected images such that they are arranged on a screen, executed by one or a plurality of computers,
the projected image display process arranging and displaying the plurality of projected images in an arrangement that corresponds to the positional relationships among the line of sight vectors,
wherein the target point setting process further comprises:
storing, in a memory, obstacle regions which are set in advance as regions that will become obstacles in ranges of view within the three dimensional region; and
judging whether each of the plurality of line of sight vectors pass through the obstacle regions or pass through the vicinities of the obstacle regions, and
wherein the projected image display process displays projected images generated for line of sight vectors which have been judged to pass through the obstacle regions or the vicinities thereof in a visually distinguishable manner from projected images generated for line of sight vectors which have been judged to not pass through the obstacle regions or the vicinities thereof,
wherein the visually distinguishable manner comprises at least one of emphasizing and marking.

3. A trocar port position determination aiding apparatus, comprising:
a memory configured to store processing instructions; and
a processor configured to execute the stored processing instructions which comprise;
a storing instruction of storing volume data obtained by imaging a subject;
a first setting instruction of setting a point within a three dimensional region represented by the volume data as a target point;

a second setting instruction of setting a three dimensional angular range having the target point as an apex and for setting a plurality of line of sight vectors within the three dimensional angular ranges directed toward the target point;

a generating and displaying instruction of generating a plurality of projected images by projecting the three dimensional regions onto projection planes perpendicular to each of the plurality of line of sight vectors, and displaying the plurality of projected images such that they are arranged on a screen in an arrangement that corresponds to the positional relationships among the line of sight vectors, wherein the storing processing instruction further comprises:

storing obstacle regions which are set in advance as regions that will become obstacles in ranges of view within the three dimensional region; and judging whether each of the plurality of line of sight vectors pass through the obstacle regions or pass through the vicinities of the obstacle regions, and wherein the displaying instruction displays projected images generated for line of sight vectors which have been judged to pass through the obstacle regions or the vicinities thereof in a visually distinguishable manner from projected images generated for line of sight vectors which have been judged to not pass through the obstacle regions or the vicinities thereof, and wherein the visually distinguishable manner comprises at least one of emphasizing and marking.

4. A trocar port position determination aiding apparatus as defined in claim 3, wherein:

the second setting instruction sets a plurality of base points within a portion of a spherical plane having a predetermined radius and the target point within the three dimensional angular range as its center, and sets vectors directed toward the target point from each of the plurality of base points as the plurality of line of sight vectors; and the displaying instructions generates the plurality of projected images by transmissive projection using the plurality of the set base points as viewpoints.

5. A trocar port position determination aiding apparatus as defined in claim 3, wherein:

the first setting instruction generates a two dimensional tomographic image or a pseudo three dimensional image based on the volume data, displays the generated image on the screen, detects a user operation that specifies a point within the two dimensional tomographic image or the pseudo three dimensional image on the screen, and sets a point within the three dimensional region corresponding to the point specified by the user operation as the target point.

6. A trocar port position determination aiding apparatus as defined in claim 3, wherein:

the second setting instruction generates at least one two dimensional tomographic image that passes through the target point, based on the volume data, detects a user operation that specifies an angular range having the target point within the at least one two dimensional tomographic image as a peak, and sets the three dimensional angular range based on the angular range specified by the user operation.

7. A trocar port position determination aiding apparatus, comprising:

a memory configured to store processing instructions; and a processor configured to execute the stored processing instructions which comprise:

a storing instruction of storing volume data obtained by imaging a subject;

a first setting instruction of setting a point within a three dimensional region represented by the volume data as a target point;

a second setting instruction of setting a three dimensional angular range having the target point as an apex and for setting a plurality of line of sight vectors within the three dimensional angular ranges directed toward the target point; and a generating and displaying instruction of generating a plurality of projected images by projecting the three dimensional regions onto projection planes perpendicular to each of the plurality of line of sight vectors, and displaying the plurality of projected images such that they are arranged on a screen in an arrangement that corresponds to the positional relationships among the line of sight vectors, wherein:

the second setting instruction detects a user operation that specifies a portion of the plurality of projected images, which are displayed on the screen, that includes two or more of the projected images, and resets a plurality of line of sight vectors directed toward target points within a portion of the three dimensional angular range that includes the line of sight vectors of the portion of the projected images specified by the user operation and include line of sight vectors different from the line of sight vectors of the portion of the projected images; and the displaying instruction generates a plurality of projected images by projecting the three dimensional region onto projection planes perpendicular to each of the plurality of reset line of sight vectors, and displays the plurality of newly generated projected images such that they are arranged on the screen.

8. A non-transitory computer readable recording medium having a trocar port position determination aiding program stored therein, the trocar port position determination aiding program causing one or a plurality of computers to execute:

a first setting instruction of setting a point within a three dimensional region represented by the volume data as a target point;

a second setting instruction of setting a three dimensional angular range having the target point as an apex and for setting a Plurality of line of sight vectors within the three dimensional angular ranges directed toward the target point; and a generating and displaying instruction of generating a plurality of projected images by projecting the three dimensional regions onto projection planes perpendicular to each of the plurality of line of sight vectors, and displaying the plurality of projected images such that they are arranged on a screen in an arrangement that corresponds to the positional relationships among the line of sight vectors, wherein:

the second setting instruction detects a user operation that specifics a portion of the plurality of projected images, which are displayed on the screen, that includes two or more of the projected images, and resets a plurality of line of sight vectors directed toward target points within a portion of the three dimensional angular range that includes the line of sight vectors of the portion of the projected images specified by the user operation and include line of sight vectors different from the line of sight vectors of the portion of the projected images; and the displaying instruction generates a plurality of projected images by projecting the three dimensional region onto projection planes perpendicular to each of the plurality of reset line of sight vectors, and displays the plurality of newly generated projected images such that they are arranged on the screen.

9. A trocar port position determination aiding method, comprising:

a first setting process, executed by at least one computer, that sets a point within a three dimensional region represented by the volume data as a target point;

a second setting process, executed by the at least one computer, that sets a three dimensional angular range having the target point as an apex and sets a plurality of line of sight vectors within the three dimensional angular ranges directed toward the target point; and a projected image display process, executed by the at least one computer, that generates a plurality of projected images by projecting the three dimensional regions onto projection planes perpendicular to each of the plurality of line of sight vectors, and displays the plurality of projected images such that they are arranged on a screen in an arrangement that corresponds to the positional relationships among the line of sight vectors, wherein:

the second setting process further detects a user operation that specifies a portion of the plurality of projected images, which are displayed on the screen, that includes two or more of the projected images, and resets a plurality of line of sight vectors directed toward target points within a portion of the three dimensional angular range that includes the line of sight vectors of the portion of the projected images specified by the user operation and include line of sight vectors different from the line of sight vectors of the portion of the projected images; and the projected image display process further generates a plurality of projected images by projecting the three dimensional region onto projection planes perpendicular to each of the plurality of reset line of sight vectors, and displays the plurality of newly generated projected images such that they are arranged on the screen.

* * * * *